United States Patent
Whisler et al.

(10) Patent No.: US 12,051,498 B2
(45) Date of Patent: Jul. 30, 2024

(54) IMAGING SYSTEM AND METHOD EMPLOYING VIRTUAL SKIN MARKERS

(71) Applicant: GE Precision Healthcare LLC, Wauwatosa, WI (US)

(72) Inventors: Doug Whisler, Seattle, WA (US); Houbing Liu, Jiangsu (CN); Yue Yang, Jiangsu (CN)

(73) Assignee: GE Precision Healthcare LLC, Wauwatosa, WI (US)

( * ) Notice: Subject to any disclaimer, the term of this patent is extended or adjusted under 35 U.S.C. 154(b) by 0 days.

(21) Appl. No.: 17/379,400

(22) Filed: Jul. 19, 2021

(65) Prior Publication Data

US 2023/0016097 A1    Jan. 19, 2023

(51) Int. Cl.
*G06F 3/04817* (2022.01)
*G06F 3/04842* (2022.01)
*G06F 3/04845* (2022.01)
*G06T 7/00* (2017.01)
*G16H 30/40* (2018.01)

(52) U.S. Cl.
CPC ......... *G16H 30/40* (2018.01); *G06F 3/04817* (2013.01); *G06F 3/04842* (2013.01); *G06F 3/04845* (2013.01); *G06T 7/0012* (2013.01); *G06T 2207/30196* (2013.01); *G06T 2207/30204* (2013.01)

(58) Field of Classification Search
CPC .................................................... G16H 30/40
See application file for complete search history.

(56) References Cited

U.S. PATENT DOCUMENTS

| 8,560,968 B1 * | 10/2013 | Nair ....................... G16H 40/63 715/810 |
| 2003/0013959 A1 * | 1/2003 | Grunwald ........... G01S 15/8981 600/437 |
| 2012/0065944 A1 * | 3/2012 | Nielsen .................. G06Q 50/06 703/1 |

(Continued)

OTHER PUBLICATIONS

Peart, "Importance of Visual Checks Before Mammograms," Imaging Technology News, May 31, 2019, accessed via Internet, [https://www.itnonline.com/article/importance-visual-checks-mammograms], 10 pages.

(Continued)

*Primary Examiner* — Di Xiao
(74) *Attorney, Agent, or Firm* — Boyle Fredrickson S.C.

(57) ABSTRACT

To document features of interest observed in a scanning procedure, after the images have been obtained the technician reviews the images on the imaging system and places virtual markers on the images (i.e., the 2D image or 3D volume) created by the imaging system. The virtual markers identify the type and location of the various features of interest observed during the imaging or scanning procedure and are placed directly on the images. Notes can also be added to the images, such as with regard to each of the virtual markers placed on the image. These virtual markers and optional notes communicate additional information regarding the patient and the image in a direct, efficient and comprehensive manner directly to the physician during later review of the images which would not be readily discernable solely from the image.

20 Claims, 8 Drawing Sheets

(56) References Cited

U.S. PATENT DOCUMENTS

| | | | |
|---|---|---|---|
| 2012/0159391 A1* | 6/2012 | Berry | A61B 5/4824 |
| | | | 715/823 |
| 2015/0005630 A1* | 1/2015 | Jung | A61B 8/468 |
| | | | 600/437 |
| 2021/0077068 A1* | 3/2021 | Lu | G06T 7/0012 |
| 2021/0100526 A1* | 4/2021 | Schein | G06T 7/251 |
| 2021/0375435 A1* | 12/2021 | O'Connor | G06F 3/0482 |

OTHER PUBLICATIONS https://www.itnonline.com/article/importance-visual-checks-mammograms, Olive Peart, "Importance of Visual Checks Before Mammograms", May 31, 2019.

* cited by examiner

IMAGING SYSTEM AND METHOD EMPLOYING VIRTUAL SKIN MARKERS

BACKGROUND OF THE INVENTION

The invention relates generally to ultrasound systems and more particularly to systems and methods to marks features in ultrasound scans for review by medical practitioners.

When obtaining images of a patient for initial screening purposes in the determination of any medical condition present within the patient being scanned, the accurate marking of any features of interest within the images is of paramount importance.

On many occasions, the images of the patient are obtained using an imaging system, such as a mammography system, a magnetic resonance imaging (MRI) system, or an ultrasound (US) system, such as an automatic breast ultrasound system (ABUS), among others, that is operated by a medical technician to create the initial image(s) for later review by the medical practitioner or radiologist. When the images are obtained by an individual that is not the individual making a diagnosis of any medical condition within the image, the forwarding of any information and/or knowledge regarding the patient and the tissue being imaged that may not be readily apparent from the obtained images to the reviewing individual/physician is not always straightforward. When imaging a breast, for example, such information can include, but is not limited to, information concerning the location of certain features of interest that have varying levels of visibility within the obtained images, e.g., the location of nipple on the breast (which can be seen), the location of moles (which can be seen) and/or scars (which potentially can be seen) on the breast, as well as the location of any palpable masses (which potentially can be seen) and/or painful or tender areas (which cannot be seen) on the breast determined as a result of the physical manipulation of the breast by the technician and/or imaging system/device performed prior to or during the scanning procedure.

In these situations, to enable the technician to provide an indication of the location and types of any features of interest that are present, as well as certain information regarding the features, prior to obtaining the images, the technician can place physical markers directly on the portion of the patient that is to be imaged. These markers have different shapes to provide rudimentary information on the particular type of feature of interest identified by the physical marker. The physical markers are formed of a material that is at least partially opaque to the energy utilized by the imaging system to create the images in order for the markers to be visible within the images of the patient obtained by the imaging system, and within any 3D volumes of the imaged portion of the patient reconstructed from the images.

However, while the physical markers positioned by the technician can be viewed in the images obtained and reconstructed volumes formed by the imaging system, the physical markers are not without significant deficiencies. For example, the placement of the markers may not be entirely accurate. In particular, the position of the marker may not be able to represent the true location of the feature being identified, such as due to movement of the physical marker or as a result of the feature being disposed at a subsurface location within the breast tissue. In these and other situations, the practitioner reviewing the markers on the images and/or volumes can only attempt to ascertain the exact location of the feature within the image or reconstructed volume using the position and location of the physical marker as a starting point for the investigation.

In addition, while the physical marker may enable a practitioner to locate a particular feature of interest, many different types of information obtained by the technician during the scanning procedure are not presented in the images and/or volumes along with the physical marker. Thus, on many occasions the information provided to the technician regarding the severity or type of pain experienced by the patient an indicated by the physical marker. Other observations by the technician, such as the appearance of any surface scar or mole, are also not readily communicated to the reviewing physician by the physical markers.

Therefore, for imaging systems when the images are initially obtained by a technician and later reviewed by a physician for diagnosis purposes, it is desirable to develop a system and method for providing visual indications or markers concerning a feature of interest disposed within an image or a volume reconstructed from the image that provides accurate and enhanced information regarding the features of interest to the reviewing physician.

BRIEF DESCRIPTION OF THE DISCLOSURE

In one exemplary embodiment of the invention, a method for providing virtual markers on a scan image of an object includes the steps of providing a scanning system including a scanning assembly for obtaining image data, a controller operably connected to the scanning assembly for controlling the operation of the scanning system, electronic memory operably connected to the controller for storing a virtual marking program executable by the controller, an image processor operably connected to the scanning assembly and configured to process images from the image data, electronic storage operably connected to the image processor for storing the image data and processed images, a display operably connected to the image processor to present the processed images, and a user interface operably connected to the controller, presenting a processed image on the display, executing the virtual marking program with the user interface and placing at least one virtual marker on the processed image.

In another exemplary embodiment of the invention, a scanning system for obtaining images of an object and transmitting the images for presentation on a remote device includes a scanning assembly for obtaining image data, a controller operably connected to the scanning assembly for controlling the operation of the scanning system, electronic memory operably connected to the controller for storing a virtual marking program executable by the controller, an image processor operably connected to the scanning assembly and configured to process images from the image data, electronic storage operably connected to the image processor for storing the image data and processed images, a display operably connected to the image processor to present the processed images, and a user interface operably connected to the controller, wherein the controller is configured to implement the virtual marking program to place one or more virtual markers directly on the processed image on the display.

In still another exemplary embodiment of, an imaging system for obtaining images of an object and transmitting the images for review on a remote device, includes a scanning system having a scanning assembly for obtaining image data, a controller operably connected to the scanning assembly for controlling the operation of the scanning system, an electronic memory operably connected to the controller for storing a virtual marking program executable by the controller, an image processor operably connected to the scanning assembly and configured to process images from the image data, electronic storage operably connected to the image processor for storing the image data and processed images, a display operably connected to the image processor to present the processed images and a user interface operably connected to the controller, and a remote workstation including a screen and operably connected to the scanning system to receive processed images stored in the electronic storage for review, wherein the controller is configured to implement the virtual marking program in response to user input through the user interface to place one or more virtual markers directly on the processed image for transmission to the remote workstation with the processed image.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

DETAILED DESCRIPTION in the present disclosure an imaging system 100 is utilized by an individual, such as an imaging technician, to obtain images of internal and external structures and/or features of interest in a portion of the body of a patient, such as a breast. The images, which can be a 2D image and/or a 3D volume reconstructed from the 2D images, are stored by the imaging system in a suitable electronic storage location for later review by a physician. During the process of obtaining the images, the technician can readily observe different features of interest on and/or within the breast, including but not limited to moles, scars, and palpable masses within the breast. The technician can additionally obtain other types of information concerning the patient, such as areas of tenderness or pain in the breast that are indicated by the patient and/or determined by the technician while performing the scans with the imaging system.

To document these features of interest, after the images have been obtained the technician reviews the images on the imaging system and places virtual markers on the images (i.e., the 2D image or 3D volume) created by the imaging system. The virtual markers identify the type and location of the various internal and/or external features of interest observed by the technician during the imaging or scanning procedure and can be placed directly on the images obtained, enabling the technician to easily position the virtual markers in the appropriate locations within the images due to the close temporal proximity for the technician between obtaining the information on the features of interest in the scanning procedure and the viewing of the images on the imaging system. The virtual markers can be positioned where desired on the image, and can optionally be altered by the technician to provide a more accurate representation of the feature of interest within the image to convey the relevant information regarding the feature of interest identified by the virtual marker to the physician who later reviews the image including the virtual markers.

In addition to the virtual markers, the technician can attach notes to or in association with the image, such as with regard to each of the virtual markers within the image. These notes can include additional information regarding the virtual marker, such as more information on the location or appearance of the feature or on the pain level or type of the feature, which would not be readily discernable solely from the image or volume. By incorporating the notes in association with the virtual markers, significant information regarding the patient and the images obtained by the technician can be communicated in a direct, efficient and comprehensive manner directly to the physician during later review of the images.

Figure 1:
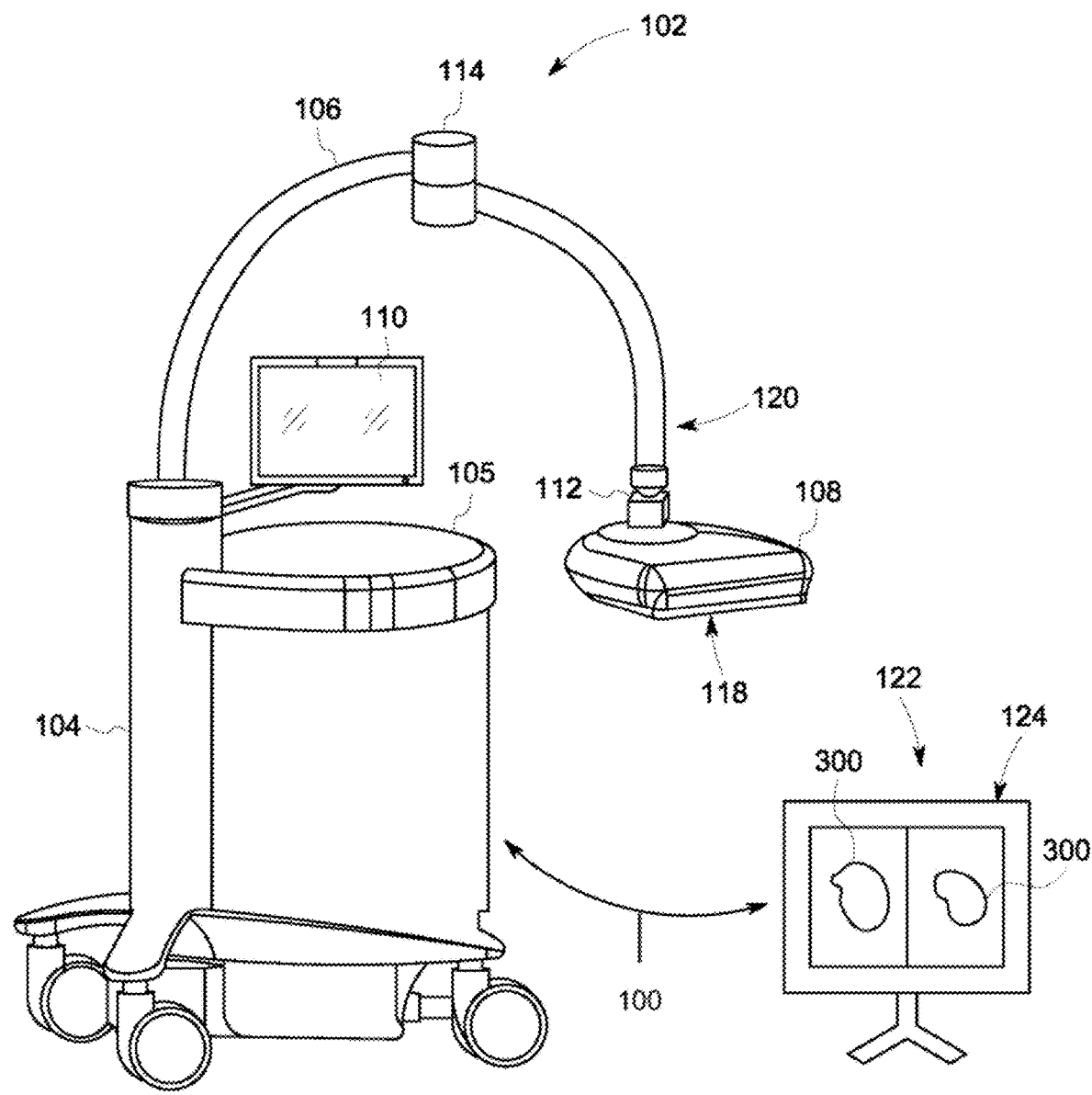
FIG. 1 shows a perspective view of a scanning apparatus according to an exemplary embodiment of the disclosure.
Figure 2:
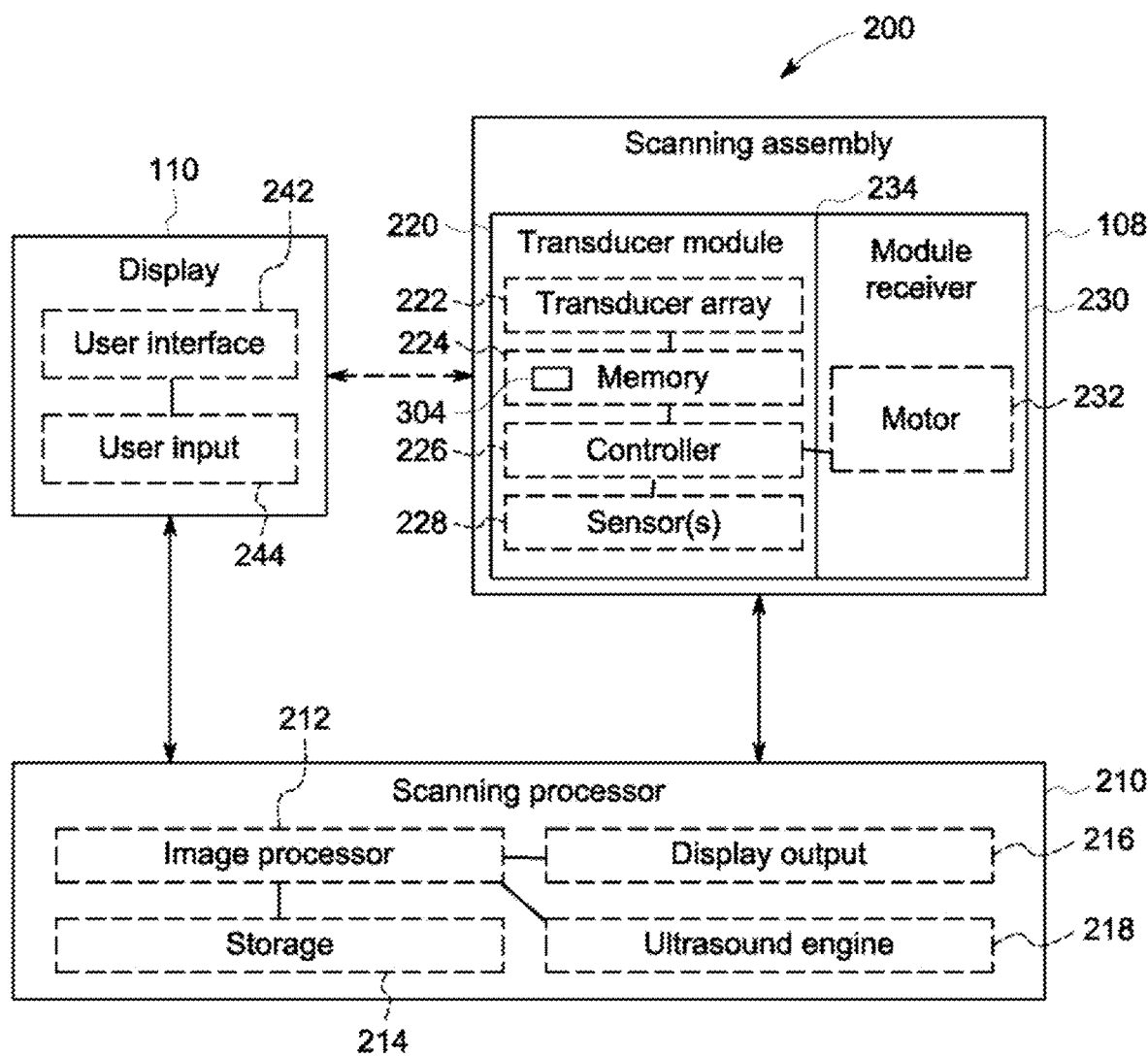
FIG. 2 shows a block schematic diagram of various system components of a scanning apparatus according to an exemplary embodiment of the disclosure.

The following description relates to patient imaging systems 100, and more specifically to breast imaging or scanning systems. FIGS. 1-2 illustrate an exemplary embodiment of an imaging system 100, such as a breast scanning system in the form of a full-field breast ultrasound (FFBU) scanning apparatus or an automated breast ultrasound system (ABUS).

In one example, a full-field breast ultrasound (FFBU) scanning apparatus, such as the ABUS scanning apparatus depicted in FIGS. 1 and 2, compresses a breast in a generally chestward or head-on direction and ultrasonically scans the breast. In another example, the FFBU scanning apparatus may compress a breast along planes such as the craniocaudal (CC) plane, the mediolateral oblique (MLO) plane, or the like. A compression/scanning assembly of the ABUS scanning apparatus may include an at least partially conformable, substantially taut membrane or film sheet, an ultrasound transducer, and a transducer translation mechanism. One side of the taut membrane or film sheet compresses the breast. The transducer translation mechanism maintains the ultrasound transducer in contact with the other side of the film sheet while translating the ultrasound transducer thereacross to scan the breast.

Typically, to maintain the transducer in contact with the film sheet and breast, a user of the transducer (such as a nurse, technician, or physician) physically applies a downward force on the transducer (e.g., in a direction toward the tissue to be scanned). In order to collect high-quality images, particularly of a dense tissue such as breast tissue, a considerably amount of force may be placed on the transducer to compress the tissue.

Although several examples herein are presented in the particular context of human breast ultrasound, it is to be appreciated that the present teachings are broadly applicable for facilitating scanning and/or imaging of any externally accessible human or animal body part (e.g., abdomen, legs, feet, arms, neck, etc.), optionally using other modalities in addition to ultrasound, such as MRI or X-ray, among others. Moreover, although several examples herein are presented in the particular context of mechanized scanning (i.e., in which the ultrasound transducer is moved by a robot arm or other automated or semi-automated mechanism), it is to be appreciated that one or more aspects of the present teachings can be advantageously applied in a handheld scanning context.

FIG. 1 illustrates a perspective view of a full field breast ultrasound (FFBU) scanning apparatus or system, or automated breast ultrasound system (ABUS) 102, hereinafter also referred to generally as scanning apparatus 102, according to an embodiment. Scanning apparatus 102 comprises a frame 104, an image or ultrasound processor housing 105 that contains an image or ultrasound processor, a movable and adjustable support arm 106 (e.g., adjustable arm) including a hinge joint 114, a compression/scanning assembly 108 connected to a first end 120 of the adjustable arm 106 via a ball-and-socket connector (e.g., ball joint) 112, and a display 110 connected to the frame 104. The display 110 is coupled to the frame 104 at an interface where the adjustable arm 106 enters into the frame 104. As a result of being directly coupled to the frame 104 and not to the adjustable arm 106, the display 110 does not affect a weight of the adjustable arm 106 and a counterbalance mechanism of the adjustable arm 106. In one example, the display 110 is rotatable in a horizontal and lateral direction (e.g., rotatable around a central axis of the frame 104), but not vertically movable. In an alternate example, the display 110 may also be vertically movable. While FIG. 1 depicts the display 110 coupled to the frame 104, in other examples the display 110 may be coupled to a different component of the scanning apparatus 102, such as coupled to the ultrasound processor housing 105, or located remotely from the scanning apparatus 102.

In one embodiment, the adjustable arm 106 is configured and adapted such that the compression/scanning assembly 108 is either (i) neutrally buoyant in space, or (ii) has a light net downward weight (e.g., 1-2 kg) for breast compression, while allowing for easy user manipulation. In alternate embodiments, the adjustable arm 106 is configured such that the compression/scanning assembly 108 is neutrally buoyant in space during positioning the scanner on the patient's tissue. Then, after positioning the compression/scanning assembly 108, internal components of the scanning apparatus 102 may be adjusted to apply a desired downward weight for breast compression and increased image quality. In one example, the downward weight (e.g., force) may be in a range of 2-11 kg.

As introduced above, the adjustable arm 106 includes a hinge joint 114. The hinge joint 114 bisects the adjustable arm 106 into a first arm portion and a second arm portion. The first arm portion is coupled to the compression/scanning assembly 108 and the second arm portion is coupled to the frame 104. The hinge joint 114 allows the second arm portion to rotate relative to the second arm portion and the frame 104. For example, the hinge joint 114 allows the compression/scanning assembly 108 to translate laterally and horizontally, but not vertically, with respect to the second arm portion and the frame 104. In this way, the compression/scanning assembly 108 may rotate toward or away from the frame 104. However, the hinge joint 114 is configured to allow the entire adjustable arm 106 (e.g., the first arm portion and the second arm portion) to move vertically together as one piece (e.g., translate upwards and downwards with the frame 104).

The compression/scanning assembly 108 comprises an at least partially conformable membrane 118 in a substantially taut state for compressing a breast, the membrane 118 having a bottom surface contacting the breast while a transducer is swept across a top surface thereof to scan the breast. In one example, the membrane is a taut fabric sheet.

Optionally, the adjustable arm may comprise potentiometers (not shown) to allow position and orientation sensing for the compression/scanning assembly 108, or other types of position and orientation sensing (e.g., gyroscopic, magnetic, optical, radio frequency (RF)) can be used. Within ultrasound processor housing 105 may be provided a fully functional ultrasound engine for driving an ultrasound transducer and generating volumetric breast ultrasound data from the scans in conjunction with the associated position and orientation information. In some examples, the volumetric scan data may be transferred from the apparatus 102/assembly 108 to another computer system, such as to a separate device or workstation 122 and display screen 124 disposed remotely from the scanning apparatus 102, for further display, review and/or processing using any of a variety of data transfer methods known in the art (e.g., wired or wireless), or the volumetric scan data may be processed by the ultrasound engine. A general purpose computer/processor, which may be integrated with the ultrasound engine, may also be provided for general user interfacing and system control. The general purpose computer may be a self-contained stand-alone unit, or may be remotely controlled, configured, and/or monitored by a remote station, such as workstation 122, connected across a network.

FIG. 2 is a block diagram 200 schematically illustrating various system components of the scanning system/apparatus 102, including the scanning assembly 108, display 110, and a scanning processor 210. Scanning processor 210 may be included within ultrasound processor housing 105 of the scanning apparatus 102 in one example. As illustrated in the embodiment of FIG. 2, the scanning assembly 108, display 110, and scanning processor 210 are separate components in communication with each other, however, in some embodiments, one or more of the components may be integrated (e.g., the display and scanning processor may be included in a single component).

Referring first to the scanning assembly 108, it comprises a transducer module 220 connected to a module receiver 230. The module receiver 230 may be positioned within a housing (attached to the arm 106 of the scanning apparatus, for example) that is configured to remain stationary during scanning, while the module receiver 230 is configured to translate with respect to the housing during scanning. In order to automatically translate with respect to the housing during scanning, the module receiver includes a motor 232 activated by the scanning processor 210, as explained below.

The transducer module 220 comprises a transducer array 222 of transducer elements, such as piezoelectric elements, that convert electrical energy into ultrasound waves and then detect the reflected ultrasound waves. The transducer module 220 is configured to be removably coupled with the module receiver 230 via a connection 234. The connection 234 may include complementary connectors on the transducer module and module receiver (e.g., a first connector on the transducer module that is configured to connect with a second connector on the module receiver) in order to establish both a mechanical connection and an electrical connection between the module receiver and the transducer module.

The transducer module 220 may further include electronic storage or memory 224. Memory 224 may be a non-transitory memory configured to store various parameters of the transducer module 220, such as transducer usage data (e.g., number of scans performed, total amount of time spent scanning, etc.), as well as specification data of the transducer (e.g., number of transducer array elements, array geometry, etc.) and/or identifying information of the transducer module 220, such as a serial number of the transducer module. Memory 224 may include removable and/or permanent devices, and may include optical memory, semiconductor memory, and/or magnetic memory, among others. Memory 224 may include volatile, non-volatile, dynamic, static, read/write, read-only, random-access, sequential-access, and/or additional memory. In an example, memory 224 may include RAM. Additionally or alternatively, memory 224 may include EEPROM.

Memory 224 may store non-transitory instructions executable by a controller or processor, such as controller 226, to carry out one or more methods or routines as described herein below. Controller 226 may receive output from various sensors 228 of the transducer module 220 and trigger actuation of one or more actuators and/or communicate with one or more components in response to the sensor output. Sensors 228 may include one or more pressure sensors and/or one or more temperature sensors. During scanning, the pressure across the scanning assembly 108 may be measured by the pressure sensors, and if the pressure distribution across the transducer module is not equal, a user may be notified (via user interface 242 of display 110, for example) to reposition the scanning assembly 108. Further, in some embodiments, to initiate scanning, motor 232 may be activated via a signal from controller 226. However, in other embodiments, motor 232 may be activated via a signal from a separate scanning processor 210, explained below.

Scanning assembly 108 may be in communication with scanning processor 210, to send raw scanning data to an image processor, for example. Additionally, data stored in memory 224 and/or output from sensors 228 may be sent to scanning processor 210 in some examples. Further, various actions of the scanning assembly 108 (e.g., translation of the module receiver 230, activation of the transducer elements, etc.) may be initiated in response to signals from the scanning processor 210. Scanning assembly 108 may optionally communicate with display 110, in order to notify a user to reposition the scanning assembly, as explained above, or to receive information from a user (via user input 224), for example.

Turning now to scanning processor 210, it includes an image processor 212, electronic storage 214, display output 216, and ultrasound engine 218. Ultrasound engine 218 may drive activation of the transducer elements of the transducer array 222 of transducer module 220 and, in some embodiments, may activate motor 232. Further, ultrasound engine 218 may receive raw image data (e.g., ultrasound echoes) from the scanning assembly 108. The raw image data may be sent to image processor 212 and/or to a remote processor (via a network, for example) and processed to form a displayable image of the tissue sample. It is to be understood that the image processor 212 may be included with the ultrasound engine 218 in some embodiments.

Information may be communicated from the ultrasound engine 218 and/or image processor 212 to a user of the scanning apparatus 102 via the display output 216 of the scanning processor 210. In one example, the user of the scanning apparatus may include an ultrasound technician, nurse, or physician such as a radiologist. For example, processed images of the scanned tissue may be sent to the display 110 via the display output 216. In another example, information relating to parameters of the scan, such as the progress of the scan, may be sent to the display 110 via the display output 216. The display 110 may include a user interface 242 configured to display images or other information to a user. Further, user interface 242 may be configured to receive input from a user (such as through user input 244) and send the input to the scanning processor 210. User input 244 may be a touch screen of or forming the display 110, in one example. However, other types of user input mechanisms are possible, such as a mouse, keyboard, etc.

Scanning processor 210 may further include storage 214. Similar to memory 224, storage 214 may include removable and/or permanent devices, and may include optical memory, semiconductor memory, and/or magnetic memory, among others. Storage 214 may include volatile, non-volatile, dynamic, static, read/write, read-only, random-access, sequential-access, and/or additional memory. Storage 214 may store non-transitory instructions executable by a controller or processor, such as ultrasound engine 218 or image processor 212, to carry out one or more methods or routines as described herein below. Storage 214 may store raw image data received from the scanning assembly 108, processed image data received from image processor 212 or a remote processor, and/or additional information, and can transmit or enable access to such data from a remote system, such as the remote workstation 120 and remote display 122.

Figure 3:
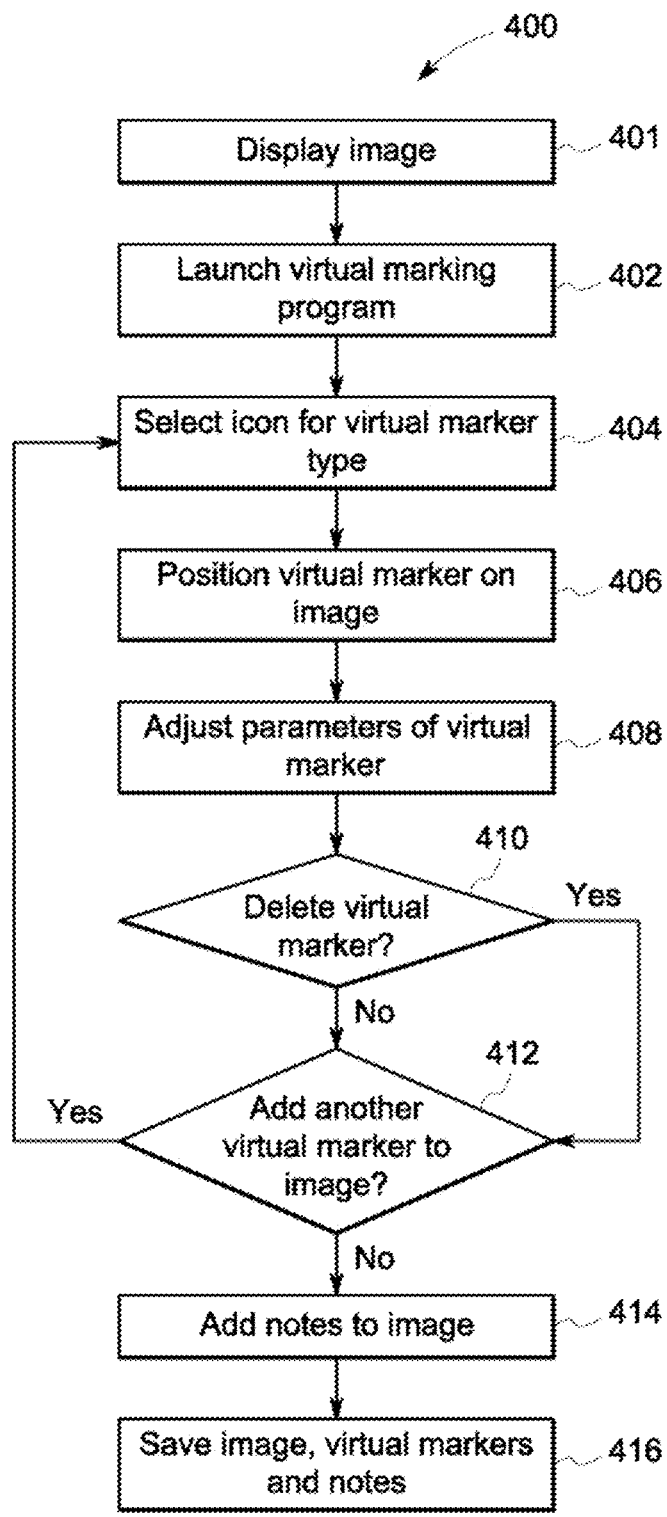
FIG. 3 is a flowchart illustrating the method of use of a virtual marking program contained on the scanning apparatus in conjunction with the image presented on the display according to an exemplary embodiment of the disclosure.
Figure 4:
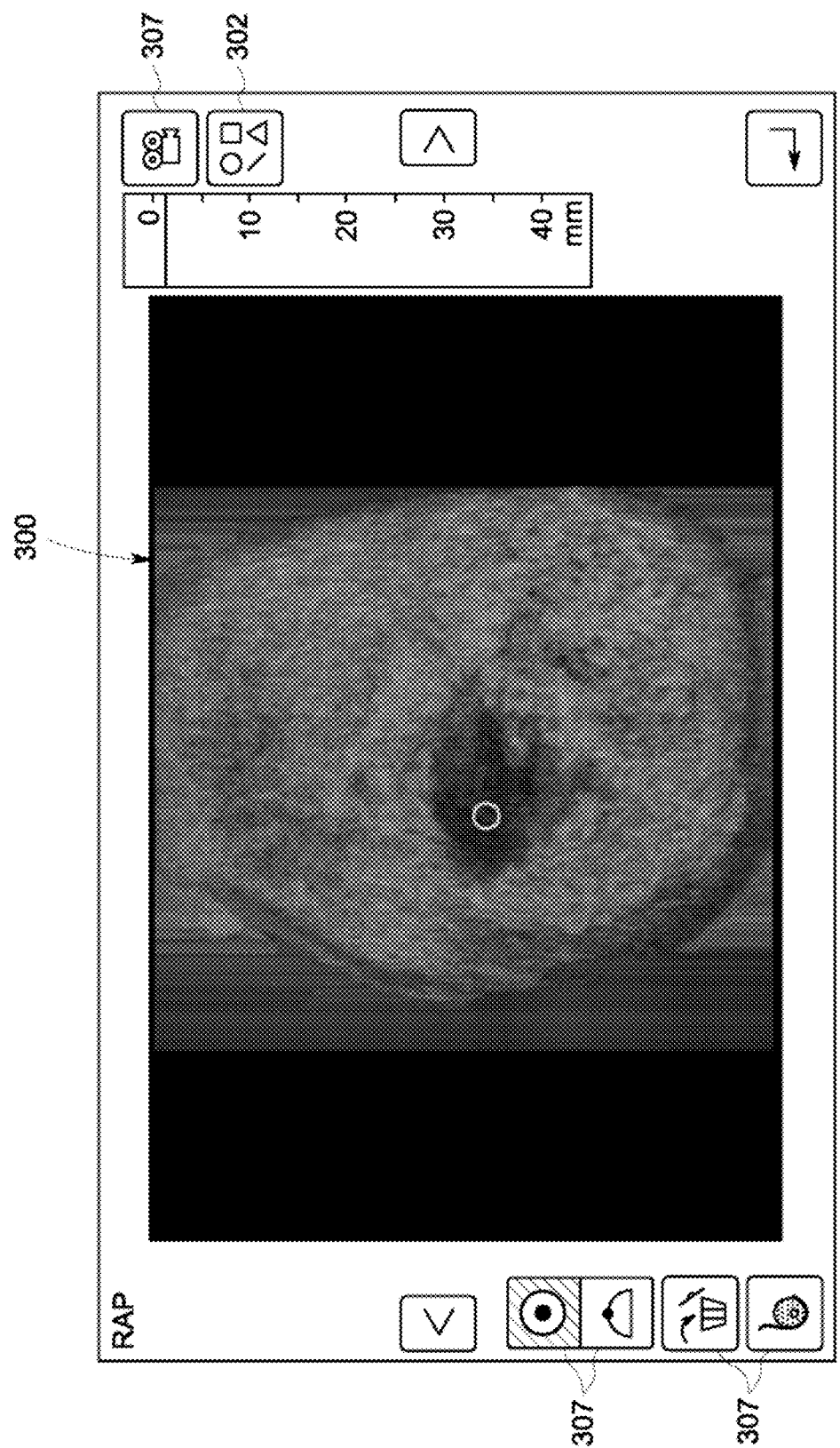
FIG. 4 is a schematic view of a user interface screen of the scanning apparatus in FIG. 2 displaying a scan image.

Looking now at FIGS. 3-8, after the image processor 212 has converted the raw image data into a set of processed images 300, which can be 2D images and/or reconstructed 3D volumes, which are retained within storage 214, in block 401 of the flowchart 400 of FIG. 3 the user can select the particular image 300 for presentation on the display 110 via the display output 216 for review by the technician on the display 110. As shown in FIG. 4, in addition to the image 300, a virtual marker/marking function button or icon 302 is presented on the display 110 in addition to other image function buttons 307. The virtual marker button 302 can be disposed in any desirable position on the display 110, and in the illustrated exemplary embodiment is located spaced from the image 300.

Figure 5:
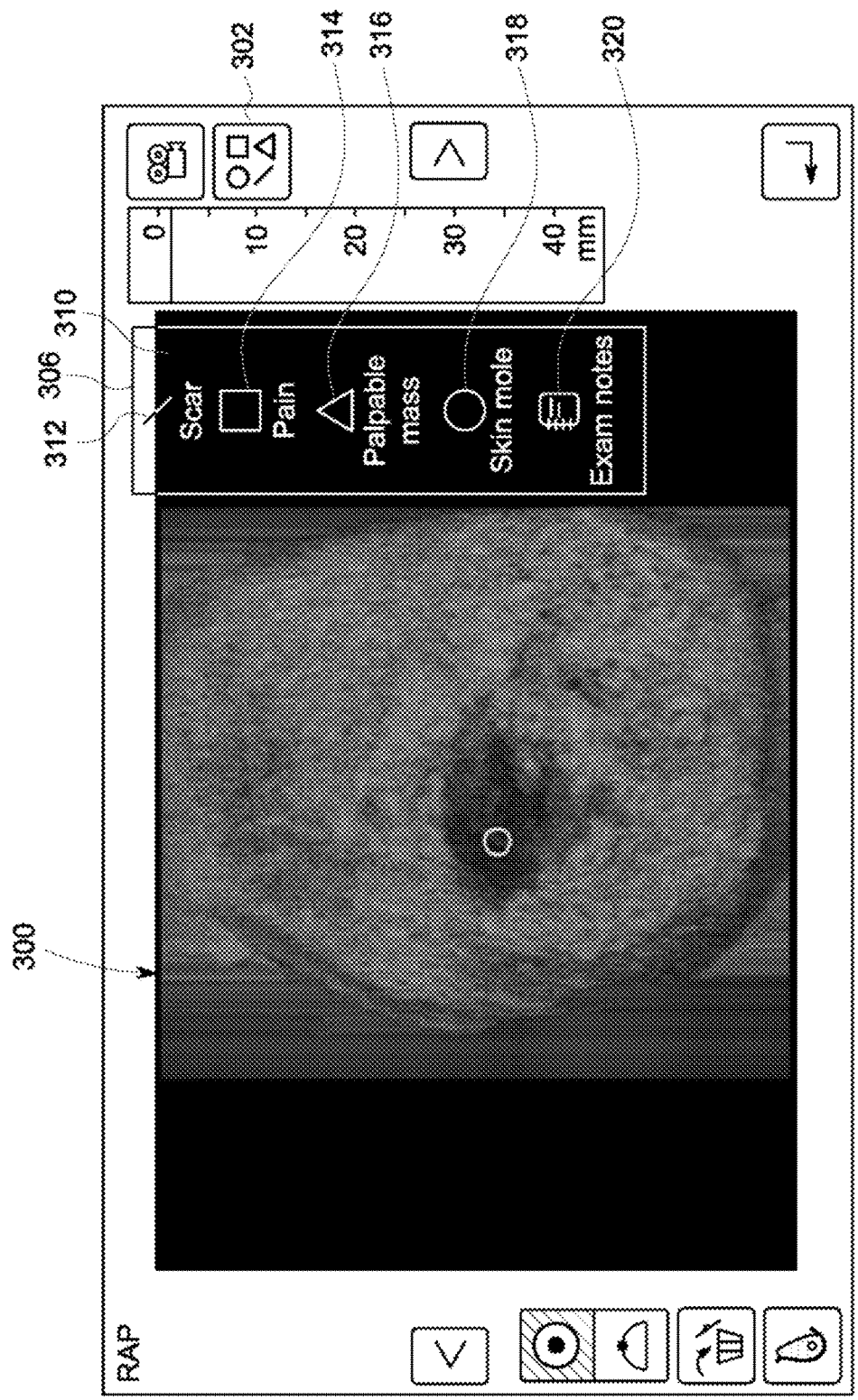
FIG. 5 is a schematic view of the user interface screen of FIG. 3 displaying a virtual marker selection menu.

Looking now at FIGS. 3 and 5, when the technician selects the virtual marker icon 302 on the display 110 through the use of the user interface 242 and/or user input 244 in block 402, the controller 226 operates to activate, launch or initiate a virtual marking program, executable or routine 304 located/stored within memory 224. As shown in FIG. 5, upon activation the virtual marking program 304 presents a virtual marker toolbar 306 on the display 110 adjacent the image 300. The toolbar 306 includes a number of representations of virtual markers 310 for the identification of different types of internal and/or external features of interest in the portion of the body, e.g., the breast, represented in the image 300, including but not limited to a scar icon 312, a pain area icon 314, a palpable mass icon 316 and a skin mole icon 318, as well as an icon (not shown) to indicate the location of the nipple within the image 300, if necessary. The toolbar 306 can also include an exam note icon 320, for a purpose to be described. Each of the representations 310 is associated with a function of the virtual marking program 304 corresponding to the type of marker indicated by the representation 310.

Figure 6:
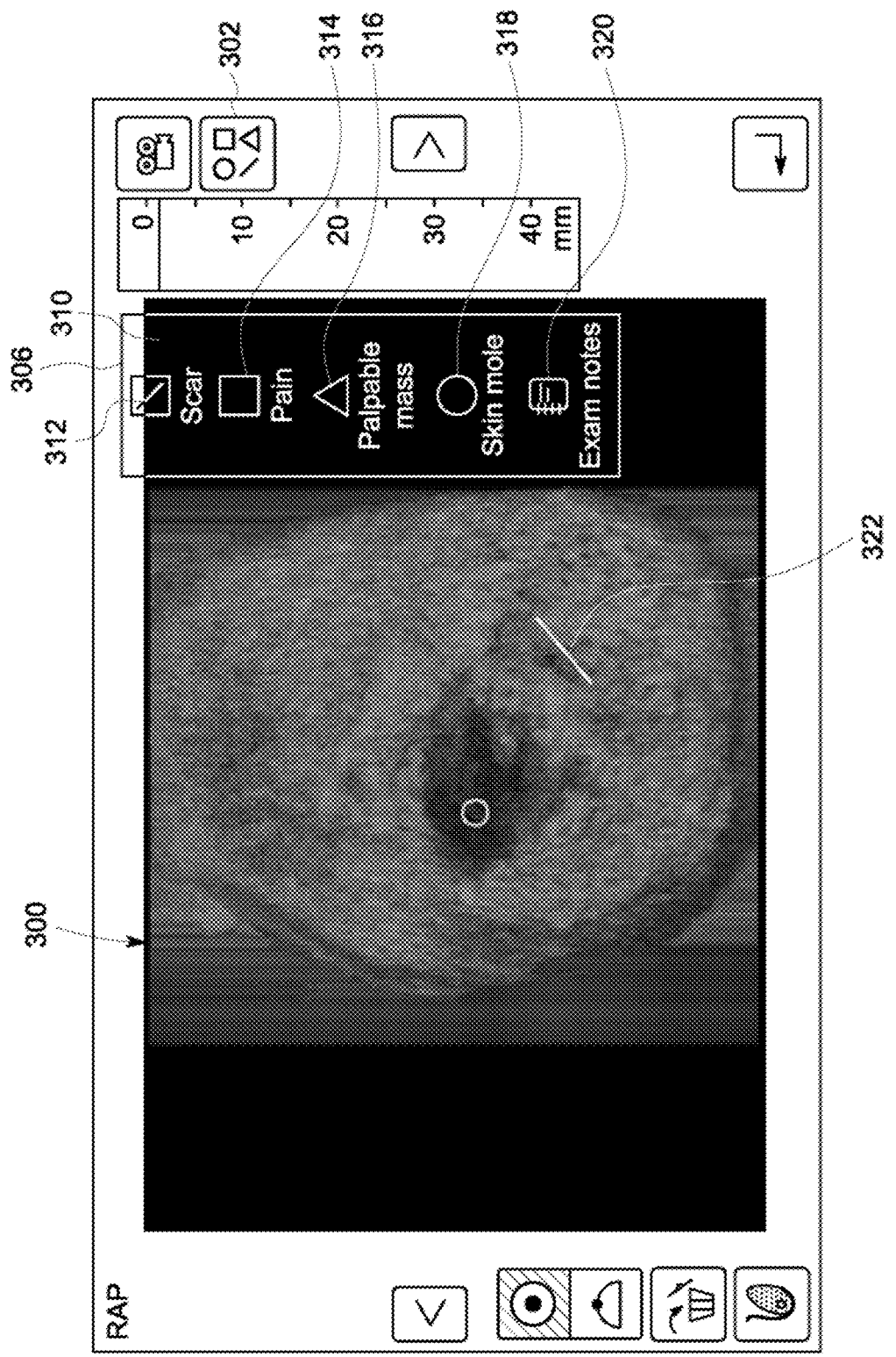
FIG. 6 is a schematic view of the user interface screen of FIG. 3 illustrating the placement of a scar virtual marker on the displayed image.
Figure 7:
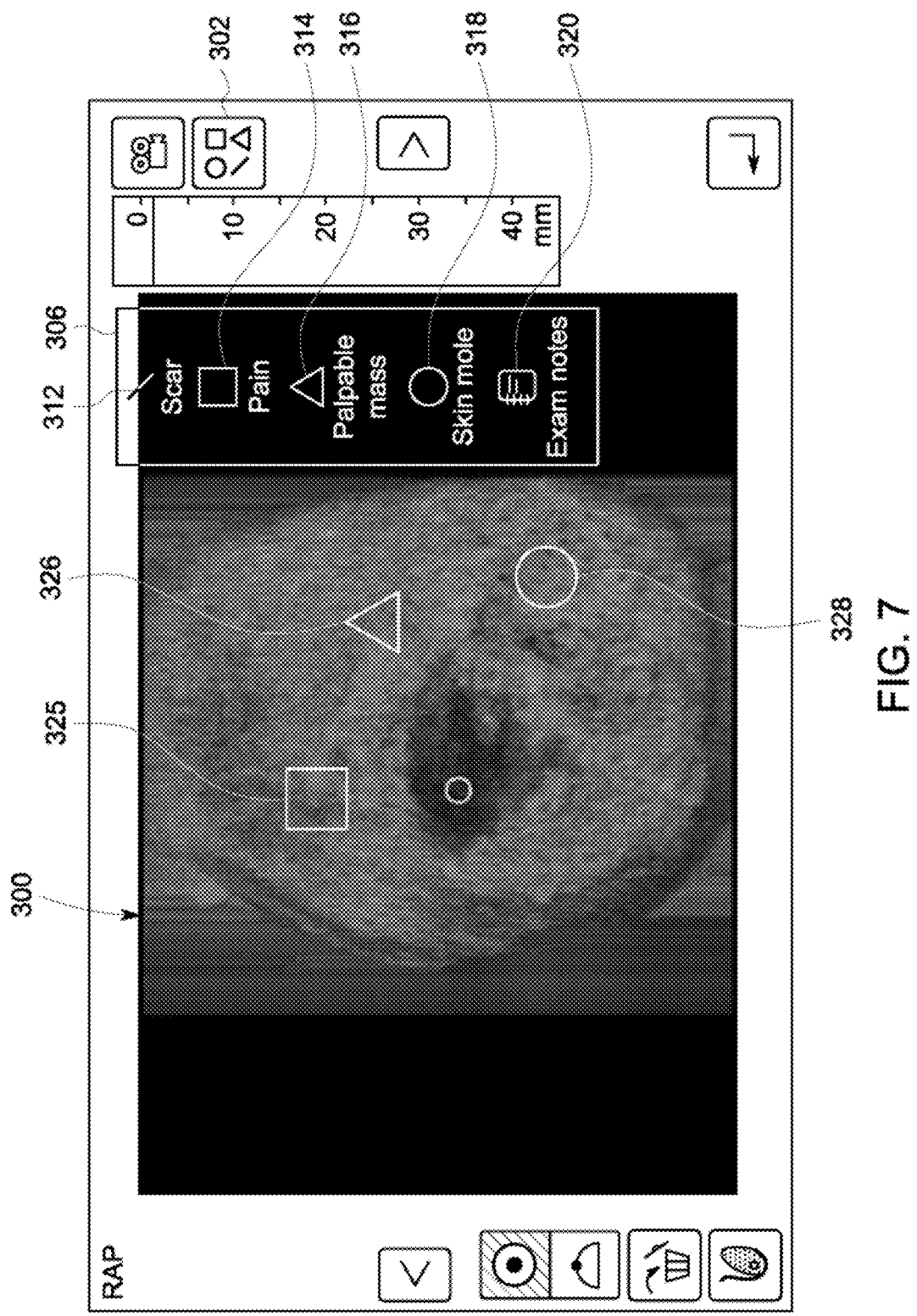
FIG. 7 is a schematic view of the user interface screen of FIG. 3 illustrating the placement of multiple virtual markers on the displayed image.

Looking now at FIGS. 3 and 6, according to one exemplary embodiment, in block 404 the user can select the representation 310/icon 312-318 associated with the particular feature of interest to be represented within the image 300. In the exemplary embodiment of FIG. 6, when the user selects the representation 310 associated with a first feature of interest on the actual patient breast to be represented virtually on the image 300. e.g., a scar, i.e., the scar icon 312, the virtual marking program 304 enables the user in block 406 to locate or place a virtual scar marker 322 directly on the image 300 presented on the display 110. In doing so, in one embodiment the virtual marking program 304 enables the user to utilize the user input/interface device 242,244 to draw the scar marker 322 on the image 300 in the location where the scar is located on the actual patient breast to provide a virtual marker for the scar directly within the image 300. Alternatively, such as in the situation where the display 110 is a touch screen and additionally functions as the user interface 242/user input 244, the virtual marking program 304 enables the user to directly contact the display 110 with a finger or a suitable stylus (not shown) and draw the scar marker 322 directly on the image 300. In still another alternative exemplary embodiment, the virtual marking program 304 can present the scar marker 322 on or near the image 300, such that the user can move the scar marker 322 onto the desired location on the image 300, such as by selecting the scar marker 322 and dragging or otherwise moving the marker 322 on the display 110 using the user interface 242/user input 244 to the desired location on the image 300.

After the scar marker 322 has been drawn, placed or otherwise disposed on the image 300, in block 408 the representation of the scar marker 322 can optionally be adjusted or manipulated by the user via the user interface 242/user input 244 to change the shape (e.g., length and/or width), size, color (such as to indicate the importance or severity of the feature of interest identified by the marker), location and/or orientation (straight and/or curved sections), among other aspects of the scar marker 322 to enable the scar marker 322 to more accurately represent the actual scar on the patient, thereby providing enhanced information to the reviewing physician regarding the scar. Where the image 300 is a 3D volume, the scar marker 322 can additionally be adjusted with regard to the depth of the scar marker 322 within the 3D volume. To adjust one or more parameters of the marker 322, the user can select the marker 322 within the image 300 through the user interface 242/user input 244, e.g. can double click on the marker 322, to indicate to the virtual marking program 304 that the parameters of the selected marker 322 are to be adjusted by the user. Once any adjustments have been completed in a suitable manner, such as those described previously, the user can again select the marker 322 to indicate to the virtual marking program 304 that the parameters of the marker 322 are to remain fixed.

Figure 8:
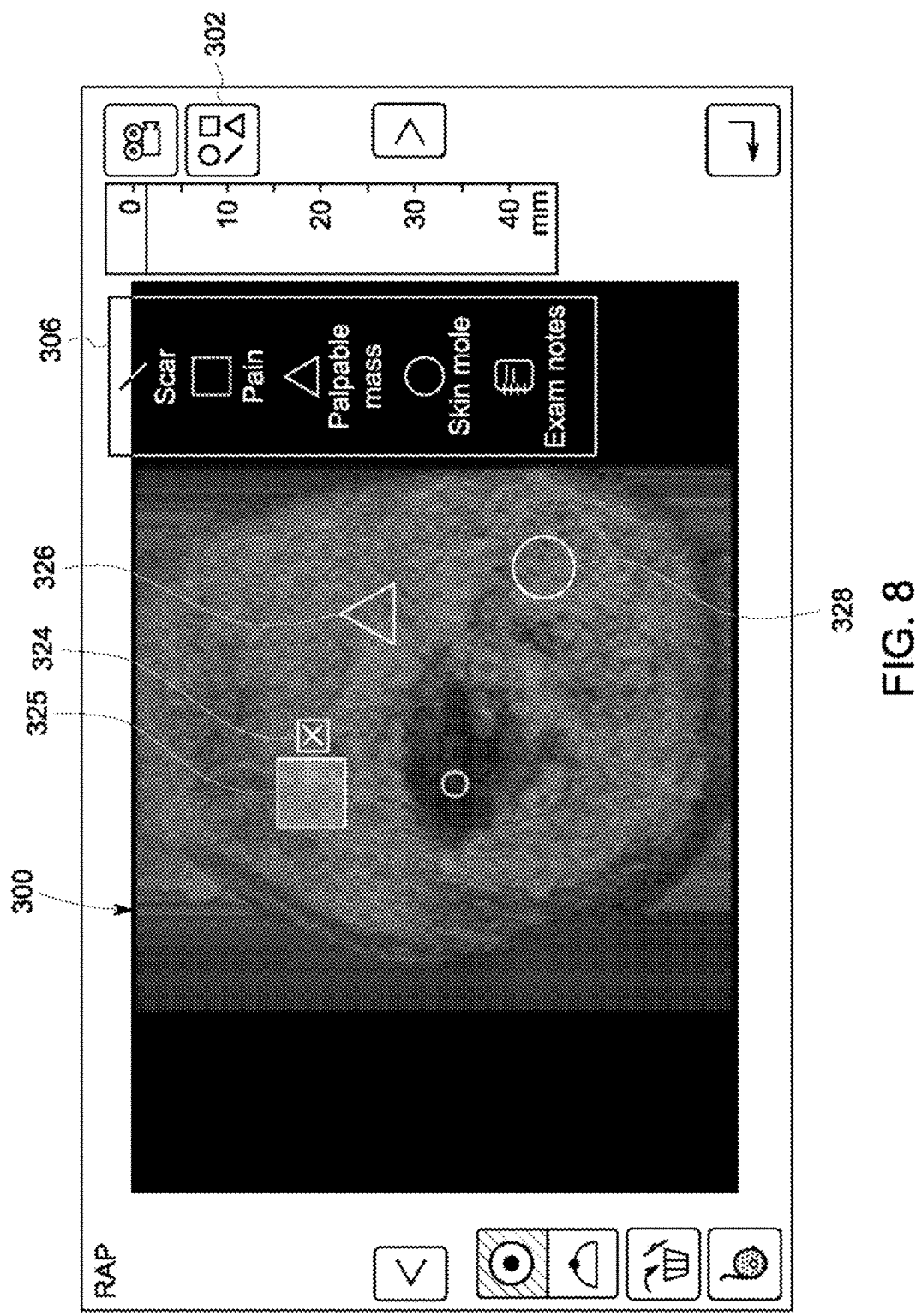
FIG. 8 is a schematic view of the user interface screen of FIG. 3 illustrating the removal of a virtual marker positioned on the image.

After or as an alternative to the adjustment of the scar marker 322 in block 408, the virtual marking program 304 allows the user to delete the scar marker 322 in block 410. As best shown in FIG. 8, to delete the scar marker 322, the user selects or clicks on the existing marker 322 within the image 300. The virtual marking program 304 subsequently highlights the marker 322 and presents a deletion button 324 on the display 110 immediately adjacent the marker 322. When the deletion button 324 is selected by the user through the user interface 242/user input 244, the virtual marking program 304 removes the marker 322 from the image 300. Alternatively, the user can select and drag the scar maker 322 off of the image 300 in order to indicate to the virtual marking program 304 that the marker 322 is to be deleted from the image 300.

Once the scar marker 322 has been positioned and adjusted within the image 300 to best approximate the location, size, shape and/or orientation of the actual scar on the patient breast, in decision block 412 the user can decide whether to return to the icon toolbar 306 and select an additional icon 312-318 in block 404 for an associated virtual marker, i.e., a virtual scar marker 322, a virtual pain area marker 325, a virtual palpable mass marker 326 or a virtual skin mole marker 328, to be placed within the image 300. In this manner, and as best illustrated in the exemplary embodiment of FIG. 7, the user can locate or position as many virtual markers 322-328 as necessary within the image 300 to provide information regarding the types and numbers of features of interest identified by the user/technician during the scanning procedure.

In addition to the virtual markers 322-328, the user can also provide a note in association with the image 300 and/or with one or more of the virtual markers 322-328 placed in the image 300 by the user in block 414. To do so, the user selected the exam note icon 320 in the toolbar 306. Upon selecting the exam note icon 320, in one exemplary embodiment the virtual marking program 304 can open a text box (not shown) on the display 110 within which the user can type or otherwise insert written summaries of the observations of the actual patient breast made by the user during the scanning procedure using the user interface 244. The text box can be associated by the virtual marking program 304 with the image 300 or with any of the virtual markers 322-328 placed on the image 300. In this manner, any information that is not readily apparent from the virtual markers 322-328 positioned on the image 300 can be easily and efficiently included with the image 300 for review along with the image 300.

After any notes to be included with the image 300 have been entered by the user, in block 416 the user can save the image 300 in an electronic data file for the image 300. In doing so, the virtual marking program 304 will store the image 300 and the various virtual markers 322-328 located on the image 300 and the notes entered by the user in a selected electronic storage location or file within the storage 214 or in any other suitable electronic storage or memory location. In that form, the image 300, virtual markers 322-328 and notes for the image 300 can be accessed in the storage 214 from the remote workstation 120 for display and review. When the image 300 is presented on the remote workstation 120 for later review, such as by a diagnosing physician, the image 300 including the virtual markers 322-328 and the associated noted are displayed such that the physician in provided with all of the information concerning the observations of the user made during the scanning procedure, thereby enhancing the transmission/minimizing the loss of any relevant information regarding the patient. In an alternative exemplary embodiment, the notes can be electronically stored in a location separate from the file in storage 214 in which the image 300 is located, but with the image 300 in addition to the virtual markers 322-328 including a notification (not shown) that notes have been entered with regard to the image 300 and where they are stored for access and review.

In the illustrated exemplary embodiments, the virtual markers 322-328 are indicated as having defined shapes corresponding to the shapes of the prior art physical markers, i.e., a line for the virtual scar marker 322, a square for the virtual pain area marker 324, a triangle for the virtual palpable mass marker 326, and a circle for the virtual skin mole marker 328. While these shaped for the virtual makers 322-328 increases the case of review by maintaining the shapes from prior art physical markers, the shapes of the virtual markers 322-328 can be altered and/or selected as desired. In addition, to enhance the ability of the virtual markers 322-328 to be visible in the image 300, the virtual markers 322-328 can be formed to be one or more colors that are the same or different form one another and the are readily apparent in the image 300. Further, the colors for the virtual markers 322-328 can be selected as desired, such as to provide additional information to the reviewing physician, such as by coding all low priority virtual markers 322-328 in green, all medium priority virtual markers 322-328 in yellow and all high priority virtual markers 322-328 in red.

With the virtual markers 322-328 disposed in the image 300 as electronically stored in storage 214 or in any other suitable accessible electronic storage location remote from the scanning apparatus 102, such as remote workstation 122, it is possible for virtual markers 322-328 disposed within different images 300 taken of the same patient at different times to be directly compared with one another, e.g., in a side-by-side or overlapping position on the display 124 of the remote workstation 122. In this manner the virtual markers 322-328 enable the reviewing physician to readily view any changes that have taken place over the time between the images 300 regarding aspects of the features of interest indicated by the virtual markers 322-328, e.g., the presence, location, size and/or orientation of the virtual markers 322-328. As such, the reviewing physician can efficiently see temporal changes in the virtual markers 322-328 within the images 300 to enhance the ability to provide accurate diagnoses for the patient based on the images 300.

The written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method for providing virtual markers on a scan image of a patient, the method comprising the steps of:
    providing a scanning system including a scanning assembly for obtaining image data, a controller operably connected to the scanning assembly for controlling the operation of the scanning system, electronic memory operably connected to the controller for storing a virtual marking program executable by the controller, an image processor operably connected to the scanning assembly and configured to process images from the image data, electronic storage operably connected to the image processor for storing the image data and processed images, a display operably connected to the image processor to present the processed images, and a user interface operably connected to the controller;
    presenting a processed image on the display;
    executing the virtual marking program with the user interface;
    placing one or more virtual markers on the processed image; and
    adding exam notes to the processed image,
    wherein the step of placing the one or more virtual markers on the processed image comprises:
        presenting a toolbar on the display including the at least one virtual marker corresponding to a feature of interest within the processed image;
        selecting an icon for at least one virtual marker; and
        positioning the one or more virtual markers on the processed image, and
    wherein one or more of the one or more markers communicates information not readily discernable from the processed image,
    wherein the toolbar includes representations of the one or more virtual markers communicating information not readily discernable from the processed image,
    wherein the representation of the one or more virtual markers communicating information not readily discernable from the processed image includes at least one of a pain icon, a scar icon, a skin mole icon and a palpable mass icon,
    wherein the representations of at least one of the pain icon, the scar icon, the skin mole icon and the palpable mass icon in the toolbar are readily discernable from one another, and
    wherein the one or more virtual markers is not associated with the exam notes.

2. The method of claim 1, wherein the processed image is selected from a 2D image and a 3D volume.

3. The method of claim 1, wherein the step of selecting the icon for the at least one virtual marker comprises:
    selecting a virtual marking program button on the display to launch the virtual marking program;
    displaying a virtual marking toolbar on the display including icons of different types of virtual markers; and
    selecting the icon for the one or more virtual markers from the toolbar.

4. The method of claim 3, wherein the step of positioning the at least one virtual marker on the processed image comprises drawing the one or more virtual markers on the processed image.

5. The method of claim 1, further comprising the step of adjusting the one or more virtual markers on the processed image after placing the one or more virtual markers on the processed image.

6. The method of claim 1, further comprising the step of saving the processed image and the one or more virtual markers in the electronic storage.

7. The method of claim 1, further comprising the step of transmitting the processed image including the one or more virtual markers from the scanning system to a remote workstation.

8. The method of claim 1, wherein the one or more virtual markers further includes one or more virtual markers associated with a particular feature of interest within the processed image.

9. A scanning system for obtaining images of an object and transmitting the images for presentation on a remote device, the scanning system comprising:
    a scanning assembly for obtaining image data, a controller operably connected to the scanning assembly for controlling the operation of the scanning system, electronic memory operably connected to the controller for storing a virtual marking program executable by the controller, an image processor operably connected to the scanning assembly and configured to process images from the image data, electronic storage operably connected to the image processor for storing the image data and processed images, a display operably connected to the image processor to present the processed images, and a user interface operably connected to the controller;

wherein the controller is configured to implement the virtual marking program to place one or more virtual markers directly on the processed image on the display, wherein the controller is configured to present the one or virtual markers on the user interface adjacent the processed image as a toolbar on the display including the one or more virtual markers each corresponding to a feature of interest within the processed image, wherein the one or more virtual markers presented in the toolbar communicates information not readily discernable from the processed image, wherein the one or more virtual markers communicating information not readily discernable from the processed image presented in the toolbar are readily discernable from one another, and wherein the one or more virtual markers disposed on different processed images are presentable in an overlapping manner.

10. The scanning system of claim 9, wherein the controller is configured to receive input from the user through the user interface to initiate the virtual marking program.

11. The scanning system of claim 10, wherein the controller is configured to provide representations of different types of the one or more virtual markers on the display for selection by the user in response to initiation of the virtual marking program.

12. The scanning system of claim 11, wherein the controller is configured to present the one or more virtual markers on the display in response to a selection by the user through the user interface.

13. The scanning system of claim 12, wherein the controller is configured to draw the one or more virtual markers on the processed image in response to input from the user through the user interface.

14. The scanning system of claim 12, wherein the controller is configured to adjust one or more parameters of the one or more virtual markers on the processed image in response to input from the user through the user interface.

15. The scanning system of claim 9, wherein the controller is configured to receive notes regarding the one or more virtual markers and the processed image provided by the user through the user interface.

16. The scanning system of claim 9, wherein the controller is configured to store the processed image and the one or more virtual markers placed thereon in the electronic storage.

17. The scanning system of claim 9, wherein the one or more virtual markers further includes one or more virtual markers associated with a particular feature of interest within the processed image.

18. An imaging system for obtaining images of an object and transmitting the images for review on a remote device, the imaging system comprising:
 a scanning system including:
  a scanning assembly for obtaining image data;
  a controller operably connected to the scanning assembly for controlling the operation of the scanning system;
  an electronic memory operably connected to the controller for storing a virtual marking program executable by the controller;
  an image processor operably connected to the scanning assembly and configured to process images from the image data;
  electronic storage operably connected to the image processor for storing the image data and processed images;
  a display operably connected to the image processor to present the processed images; and
  a user interface operably connected to the controller; and
 a remote workstation including a screen and operably connected to the scanning system to receive processed images stored in the electronic storage for review, wherein the controller is configured to implement the virtual marking program in response to user input through the user interface to place one or more virtual markers directly on the processed image for transmission to the remote workstation with the processed image, wherein the controller is configured to present the one or virtual markers on the user interface adjacent the processed image as a toolbar on the display including the one or more virtual markers each corresponding to a feature of interest within the processed image and to enable the one or more virtual markers to be moved onto the processed image in response to input from the user through the user interface, wherein one or more of the virtual markers presented in the toolbar communicates information not readily discernable from the processed image, wherein the one or more virtual markers communicating information not readily discernable from the processed image presented in the toolbar includes one or both of a pain icon and a palpable mass icon, wherein the representation of the one or more virtual markers communicating information not readily discernable from the processed image includes at least one of a pain icon, a scar icon, a skin mole icon and a palpable mass icon, wherein the representations of at least one of the pain icon, the scar icon, the skin mole icon and the palpable mass icon in the toolbar are readily discernable from one another, and wherein the one or more virtual markers disposed on different processed images are presentable in an overlapping manner.

19. The imaging system of claim 18, wherein the controller is configured to receive notes regarding the at processed image and the one or more virtual markers through the user interface for transmission to the remote workstation with the processed image and the one or more virtual markers.

20. The imaging system of claim 18, wherein the one or more virtual markers further includes one or more virtual markers associated with a particular feature of interest within the processed image.

* * * * *